United States Patent
Ashida et al.

[11] Patent Number: 5,891,811
[45] Date of Patent: Apr. 6, 1999

[54] INDICATOR MATERIAL

[75] Inventors: Tetsuya Ashida, Nagaokakyo; Masayoshi Ikezawa, Kita-Saitama-gun, both of Japan

[73] Assignees: Mitsubishi Paper Mills Ltd.; Hakugen Co., Ltd., both of Tokyo, Japan

[21] Appl. No.: 750,908
[22] PCT Filed: Jul. 24, 1995
[86] PCT No.: PCT/JP95/01470
   § 371 Date: Apr. 11, 1997
   § 102(e) Date: Apr. 11, 1997
[87] PCT Pub. No.: WO96/03638
   PCT Pub. Date: Feb. 8, 1996

[30] Foreign Application Priority Data

Jul. 22, 1994 [JP] Japan ..................... 6-170665
Aug. 10, 1994 [JP] Japan ..................... 6-188037
Sep. 7, 1994 [JP] Japan ..................... 6-213384

[51] Int. Cl.$^6$ .................................... B32B 27/04
[52] U.S. Cl. .............. 442/71; 442/67; 442/123; 442/125; 442/164; 442/351
[58] Field of Search ................ 442/64, 67, 71, 442/123, 125, 164, 351

[56] References Cited

FOREIGN PATENT DOCUMENTS

| 60-51101 | 3/1985 | Japan. | |
| 2-118181 | 5/1990 | Japan. | |
| 5-14983 | 2/1993 | Japan. | |
| 6-033361 | 2/1994 | Japan | D04H 11/08 |
| 6-75739 | 10/1994 | Japan. | |
| 6-322652 | 11/1994 | Japan | D04H 3/00 |

*Primary Examiner*—Christopher Raimund
*Attorney, Agent, or Firm*—Frishauf, Holtz, Goodman, Langer & Chick, P.C.

[57] ABSTRACT

The present invention is concerned with an indicator material which is obtained by impregnating a non-woven fabric, of which one surface is provided with a resin layer having a partly or wholly colored surface, with a volatile oily substance used as an active ingredient in a deodorant, an aromatic agent, an anti-fungal agent or a mothproofing agent, and which is used for showing the degree of dissipation of the oily substance which occurs with the passage of time, based on the shifting of the resin layer observable from the non-woven fabric side from a visible state to a state masked by the non-woven fabric, the indicator material overcoming a failure of conventional indicator materials containing non-woven fabrics in relatively clearly showing the degree of the oily substance with the passage of time, by using a non-woven fabric containing a fine-denier fiber having a size of 2 denier or less or by using a non-woven fabric having a partly altered density.

31 Claims, 3 Drawing Sheets

INDICATOR MATERIAL

TECHNICAL FIELD

The present invention relates to an indicator material for indicating the degree of dissipation of a volatile oily substance which occurs with the passage of time, the volatile oily substance being contained, an active ingredient, in a deodorant, an aromatic agent, an anti-fungal agent, an insecticide, a mothproofing agent, and the like. In particular, it relates to an indicator material which is prepared by impregnating a non-woven fabric with the above oily substance and which indicates the degree of such a dissipation of the above oily substance as occurs with the passage of time.

TECHNICAL BACKGROUND

The deodorant, aromatic agent, anti-fungal agent, insecticide, mothproofing agent, and the like, which are prepared by providing oily substances having volatility at room temperature or an increased temperature as active ingredients and impregnating predetermined carriers with the active ingredients, have been and are used as substitutes for conventional articles containing volatile gels or solids as active ingredients. Most of the above oily substances are odorless, and when they are used by impregnating carriers with the above odorless oily substances, it is difficult to ascertain even the time of expiration thereof, not to mention the remaining content thereof, by the human sense of smell. For this reason, there have been developed a variety of indicator materials which can visually show users the remaining time and the expiration time of the oily substances.

Among the above indicator materials are the following two indicator materials each of which is prepared by impregnating a non-woven fabric with the above oily substance and can visually show users the degree of the dissipation thereof which occurs with the passage of time.

One is a mothproofing material which also works as a mothproofing capability indicator, in which one surface of an oil-permeable paper-like material (including a non-woven fabric), which is altered into transparency when an oil (oily substance) is contained, is used as an indicating surface, an oil-impermeable pattern layer is formed on the entirety or part of the other surface of the paper-like material to obtain a substrate and the substrate is impregnated with an oil mothproofing agent volatile at room temperature (JP-B-4-36122).

In the above mothproofing material which also works as a mothproofing capability indicator, since the paper-like material is altered into transparency when an oil mothproofing agent is contained, the pattern layer provided on the other side can be visually observed. On the other hand, since the paper-like material is gradually brought into an original non-transparent state with the dissipation of the liquid oil, the pattern layer formed on the other side gradually becomes visually non-observable. Depending upon the pattern layer visually observable from the paper-like material side, therefore, users can visually know the degree of dissipation of the liquid oil (mothproofing chemical) which occurs with the passage of time.

The other one is a time length indicator prepared by consecutively applying a colorant, which is altered into transparency when a liquid volatile at room temperature penetrates it, to portions where the above contained liquid is dissipated earlier and later on the surface of a substrate sheet (including a non-woven fabric) into which a liquid containing the liquid volatile at room temperature is penetrable, such that the colorant form layers as time length indicating layers (Japanese Laid-open Utility Model Publication No. 5-14983). The above time length indicator uses the fact that when the substrate sheet containing the liquid volatile at room temperature is held horizontally, the liquid volatile at room temperature is easily successively dissipated from an edge portion of the substrate sheet surface and that when the substrate sheet containing the liquid volatile at room temperature is held vertically, the liquid volatile at room temperature is easily successively dissipated from the top of the substrate sheet. The time length indicator having a predetermined form is provided depending upon a pre-determined method of setting the time length indicator.

When the liquid is contained in the substrate sheet of the above time length indicator, the time length indicating layers show a transparent state, since the liquid penetrate the time length indicating layers. With the dissipation of the liquid contained in the substrate sheet, the amount of the liquid which has penetrated the time length indicating layers decreases, and the time length indicating layers accordingly become visually observable. Users can therefore know the degree of the dissipation of the liquid which occurs with the passage of time depending upon which time length indicating layer can be visually observed.

When a conventional non-woven fabric is impregnated with an oily substance volatile at room temperature or an increased temperature, the dissipation of the oily substance from the non-woven fabric does not take place uniformly. Therefore, when a conventional non-woven fabric is used as a paper-like material to prepare an indicator material having the same constitution as that of the above mothproofing material which also works as a mothproofing capability indicator, the pattern layer formed on the other side of the paper-like material becomes visually non-observable with the dissipation of the oily substance, while the visual sight thereof differs from one place to another on the paper-like material (non-woven fabric) and a spots-like pattern is observed. It is therefore difficult to clearly show the degree of dissipation of the oily substance which occurs with the passage of time with the above indicator material.

Further, a conventional non-woven fabric has the relatively low capacity to support the oily substance. That is, when the non-woven fabric is impregnated with the oily substance in an amount equivalent to, or smaller than, the volume of pores of the non-woven fabric, the capacity of the non-woven fabric to support the oily substance such that the oily substance does not seep is relatively low. Therefore, when a conventional non-woven fabric is used to prepare an indicator material having the same constitution as that of the above mothproofing material which also works as a mothproofing capability indicator, the indicator material can contain only a relatively small amount of the oily substance.

On the other hand, a conventional non-woven fabric is used as a substrate sheet to prepare an indicator material having the same constitution as that of the above time length indicator, the time length indicator layers do not relatively clearly show the degree of dissipation of the oily substance which occurs with the passage of time. Further, this indicator material can contain only a small amount of the oily substance. Moreover, when the indicator material is set by a method which is not predetermined when it is prepared, for example, when it is set slantly or upside down, the time length indicating layer showing a time length different from the time length which has actually passed is visually observed, and the setting site and the setting method are therefore limited.

It is an object of the present invention to provide an indicator material which can clearly indicate not only the time of expiration of the oily substance but also the degree of dissipation of the oily substance which occurs with the passage of time, regardless of a setting site and a setting method.

DISCLOSURE OF THE INVENTION

The indicator material for achieving the above object, provided by the present invention, is provided by forming a resin layer having a surface partly or wholly colored on one surface of a support formed of a non-woven fabric containing a fine-denier fiber having a size of 2 denier or less, said support having a low refractive index to light, and impregnating the support with an oily substance volatile at room temperature or increased temperature, characterized in that the resin layer observed from the support side is shifted from a visible state to a support-masked state by the dissipation of the oily substance which occurs with the passage of time (the above indicator material will be referred to as "indicator material I" hereinafter).

Another indicator material for achieving the above object, provided by the present invention, is provided by forming a resin layer having a surface partly or wholly colored on one surface of a support formed of a non-woven fabric having a partly altered density and having a low refractive index to light, and impregnating the support with an oily substance volatile at room temperature or increased temperature, characterized in that the resin layer observed from the support side is shifted from a visible state to a support-masked state by the dissipation of the oily substance which occurs with the passage of time (the above indicator material will be referred to as "indicator material II" hereinafter).

PREFERRED EMBODIMENTS OF THE INVENTION

Figure 5:
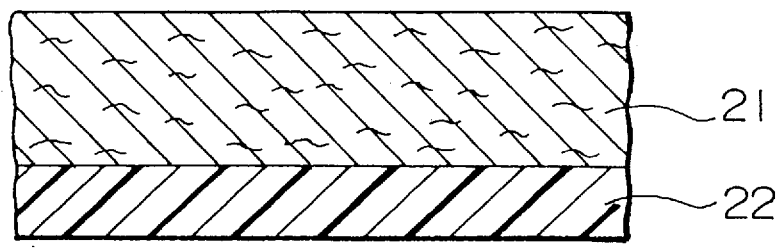
FIG. 5 is a schematic cross-sectional view of a preferred embodiment of an indicator material I.

As schematically shown in FIG. 5, the indicator material I of the present invention is a material prepared by forming a resin layer 22 having a surface partly or wholly colored on one surface of a support 21 which is formed of a non-woven fabric containing a fine-denier fiber having a size of 2 denier or less and has a low refractive index to light and impregnating the support 21 with an oily substance (not shown) volatile at room temperature or increased temperature. The term "non-woven fabric having a low refractive index to light" means that a fiber constituting the above non-woven fabric has a low refractive index, and the refractive index value is preferably 2.0 or less, more preferably 1.7 or less.

The non-woven fabric can be that which is basically non-transparent but substantially becomes transparent when impregnated with an oily substance volatile at room temperature or increased temperature, to be described later, so that a color of the resin layer (color of a colored portion) provided on one surface of the above non-woven fabric can be easily observed from the non-woven fabric side. The refractive index of a fiber constituting the above non-woven fabric is preferably similar to the refractive index of the oily substance to be used for the impregnation, while the non-woven fabric may contain a substantially non-transparent fiber so long as the non-woven fabric as a whole becomes transparent when it is impregnated with the oily substance.

The reason for limiting the non-woven fabric as a support to the "non-woven fabric containing a fine-denier fiber" having a size of 2 denier or less" is as follows. That is, when the non-woven fabric is constituted of a fiber having a size of more than 2 denier, the fiber has a low capacity to support the oily substance among its filaments, and the oily substance is therefore liable to leak even if the non-woven fabric is impregnated with the oily substance. In particular, when the indicator material is placed perpendicular to the ground surface or suspended, the oily substance is liable to run downward. However, when the non-woven fabric contains the above fine-denier fiber, the oily substance can be supported more uniformly and firmly, and the oily substance with which the non-woven fabric is impregnated can be more uniformly dissipated. When the oily substance is uniformly dissipated, the process of the resin layer shifting from a visible state to a masked state uniformly takes place in the indicator material as an end product shifting, and a color change in the indicator material is clear. As a result, the amount of the oily substance remaining with the passage of time can be more clearly indicated. The indicator material I therefore uses the "non-woven fabric containing a fine-denier fiber having a size of 2 denier or less" as a support.

The content of the above "fine-denier fiber having a size of 2 denier or less" in the non-woven fabric is preferably 9 to 100% by weight, particularly preferably 20 to 100% by weight. Further, the size of the above fine-denier fiber is preferably 1 denier or less.

For obtaining a non-woven fabric which can support the oily substance volatile at room temperature or increased temperature, to be described later, as uniformly as possible, the fine-denier fiber is preferably a synthetic fiber of which the form is constant and stand-like, and it is particularly preferably a synthetic fiber of acryl, polyester, polypropylene, vinylone or nylon. The above fine-denier fiber may be a non-transparent fiber such as a fiber containing a white pigment (SD: semi-dull, D: dull) so long as there can be finally obtained a non-woven fabric which is basically non-transparent but becomes substantially transparent when impregnated with the oily substance, while the fine-denier fiber is preferably a substantially transparent fiber containing no or almost no white pigment such as titanium dioxide (SB: super bright, B: bright). A substantially transparent fiber and a non-transparent fiber may be used in combination.

The non-woven fabric containing the above fine-denier fiber may be a non-woven fabric produced by any method, while a non-woven fabric produced by a wet paper making method is more preferred than that produced by a dry method in which a non-woven fabric having a relatively low density can be produced, since a greatly uniform non-woven fabric can be produced and since the density of the non-woven fabric can be easily adjusted. The above term "wet paper making method" refers to a method in which a fiber is dispersed in water to form a solution having a low concentration of the fiber, additives such as dispersing agent, a thickener and a flocculating agent are added as required, and then a non-woven fabric is produced with a cylinder paper machine, a Fourdrinier paper machine, an inclined paper machine or a combination paper machine made of at least two paper machines. When the non-woven fabric is produced by the wet paper making method, a non-woven fabric excellent in fiber distribution, i.e., formation. When such a non-woven fabric is impregnated with the oily substance to be described later, the distribution of the oily substance is uniform, and the degree of dissipation of the oily substance is therefore made more uniform. As a result, in the indicator material as an end product, the process of the resin shifting from a visible state to a masked state takes place more uniformly, and the alteration for the indicator material becomes more clear.

When the non-woven fabric is produced, the above described fine-denier fiber alone may be used. Otherwise, a fiber other than the fine-denier fiber, such as a fiber having a binder function, a synthetic fiber having a size of greater than 2 denier or a natural fiber such as wood pulp, cotton or hemp may be used in combination. In particular, a fiber having a binder function is preferred for imparting the non-woven fabric with strength. As a binder fiber, preferred are a heat-fusable fiber of which filaments are partially or wholly softened or melted to be fused to adjacent filaments, and a vinylon-containing binder fiber of which filaments are partially or wholly melted with hot water and are mutually bonded when it is dried. On the other hand, when a natural fiber is used in combination, it is difficult to completely wet the natural fiber with the oily substance to be described later, or portions not wetted with the oily substance become non-transparent in white, and the amount thereof for use is therefore properly selected for obtaining a non-woven fabric which substantially becomes transparent when impregnated with the oily substance to be described later.

The non-woven fabric used for constituting the indicator material I may contain a substance having a low refractive index to light, such as an inorganic pigment typified by porous silica, for permitting the observation of a more clear process of the resin layer shifting from a visible state to a masked state in the indicator material as an end product. The produced non-woven fabric may be subjected to a post treatment such as heat treatment, impregnation with a resin or calender treatment for imparting it with desired properties. When the non-woven fabric is produced by a wet paper making method, the produced non-woven fabric may be subjected to a post treatment by a carding method, a needle punching method or a spun lacing method for the purpose of further increasing the strength of the non-woven fabric by the mutual entanglement of filaments constituting the non-woven fabric.

Although differing depending upon the amount of the oily substance to be used for the impregnation, the basis weight of the above non-woven fabric is generally preferably 20 to 200 g/m². Further, the density of the non-woven fabric is preferably 0.1 to 0.5 g/cm³. When the density is lower than 0.1 g/cm³, undesirably, the non-woven fabric is poor in the capacity to support the oily substance and liquid may sag. When the density is higher than 0.5 g/cm³, there is no difference in the capacity to support the oily substance, but the amount of the oily substance supported per unit area decreases and an indicator material (non-woven fabric) having a very large area is therefore required to obtain a practical indicator material I. Since the amount of the oily substance supported in the non-woven fabric per unit area is generally smaller than the non-woven fabric space volume of the non-woven fabric, the non-woven fabric space volume of the non-woven fabric used for constituting the indicator material I is preferably at least 50 cm³/m², particularly preferably 50 to 1,800 cm³/m², in practical use. The term "non-woven fabric space volume" used in the present invention refers to a value determined on the basis of the following equation.

$$NS = G(1/D - 1/FD)$$

NS: Non-woven fabric space volume (cm³/m²)
G: Basis weight of non-woven fabric (g/m²)
D: Density of non-woven fabric (g/cm³)
FD: Density of fiber (g/cm³)

In the indicator material I, a resin layer having a partly or wholly colored surface is formed on one surface of the above non-woven fabric. The resin layer is required to have resistance against the oily substance used for impregnating the above non-woven fabric, and a resin soluble in the oily substance used for impregnating the above non-woven fabric is not preferred. The resin layer is preferably a layer formed of a thermoplastic resin in view of easiness in processing and easiness in coloring or printing. Polyolefin resins are particularly preferred as a raw material for the resin layer, since they have resistance to almost all oily substances and have suitability for melt lamination and the capability of forming a uniform film. Among the polyolefin resins, more preferred are a polyethylene resin and a polypropylene resin.

Specific examples of the method of forming the above resin layer having a partly or wholly colored surface includes the following methods (1) and (2).

(1) A method in which one surface of the non-woven fabric is provided with a coating resin layer to coat said one surface, and the surface of the resin layer is colored by a printing method using a coloring ink, or the like.

The formation of the above coating resin layer by the above method can be carried out by an application method, a method using an adhesive, or a melt extrusion application method.

In the above application method, for example, the above coating resin layer can be formed by dissolving a resin in a solvent to prepare a coating solution, applying the coating solution to one surface of the non-woven fabric and drying the resultant coating. In the method using an adhesive, for example, the above coating resin layer can be formed by bonding a resin film to one surface of the non-woven fabric by a dry laminating method or a wet laminating method. In the melt extrusion application method, for example, the above coating resin layer can be formed by melt-extrusion-applying a thermoplastic resin to one surface of the non-woven fabric.

(2) A method in which a coating resin layer having an entirely colored surface is directly formed on one surface of the non-woven fabric.

In the above method, the above coating resin layer having an entirely colored surface can be formed by a method using an adhesive or a melt extrusion application method.

In the method using an adhesive, for example, the coating resin layer having an entirely colored surface can be formed by bonding a resin film having an entirely colored surface to one surface of the non-woven fabric by a dry laminating method or a wet laminating method. Further, in the melt extrusion application method, for example, the above coating resin layer having an entirely colored surface can be formed by melt-mixing a colorless thermoplastic resin and a master batch prepared by dispersing a high concentration of a coloring pigment such as ultramarine, cobalt blue or the like in an extrusion application machine and melt-extrusion-applying the mixture to one surface of the non-woven fabric.

In both the above-described methods (1) and (2), a melt-application method is preferred since a resin layer which is uniform and free of pin holes can be obtained.

The indicator material I of the present invention is obtained by forming the above resin layer on one surface of the above non-woven fabric and impregnating the non-woven fabric with an oily substance volatile at room temperature or increased temperature. The term "oily substance volatile at room temperature" in the present invention refers to an oily substance which volatilizes at an ambient temperature at which the indicator material is used, without heating the indicator material as an end product or without heating the ambiance in a site where the indicator material is used. The term "oily substance volatile at an increased temperature" refers to an oily substance which does not volatilize without heating the indicator material as an end product by proper heating means in an ambiance in a site where the indicator material is used. The oily substance volatile at room temperature and the oily substance volatile at an increased temperature having common meanings in the indicator material I of the present invention and the indicator material II to be described later.

Depending upon the use of the indicator material I as an end product, the above oily substance volatile at room temperature or increased temperature is selected, for example, from oily aromatic agents, oily deodorants, oily mothproofing agents, oily insecticides, and the like, which are volatile at room temperature or increased temperature.

Specific examples of the oily aromatic agents and the oily deodorants volatile at room temperature or increased temperature include those containing a component such as benzaldehyde, α-pinene, geraniol, citronellal, linalool, limonene, linalyl mentholacetate, amylcinnamic aldehyde, methyl anthranilate, isoeugenol, allyl caproate, isobutyl acetate, benzyl acetate, isoamyl salicylate, citral, decyl aldehyde, hydroxycitronellal, isoamyl acetate, or the like, and plant essential oils having aromatic deodorization effects such as bitter almond, hinoki oil, nutmeg oil, geranium oil, lavender oil, lime oil, peppermint oil, vetiver oil, sweet orange oil and thyme oil.

As specific examples of the oily mothproofing agents or the oily insecticides volatile at room temperature or increased temperature mothproofing agents include those containing a component such as α-pinene, eugenol, thujone, thymol, hinokitiol, cinnamic aldehyde, carvacrol, or the like, volatile pyrethroid insecticides such as empenthrin, allethrin, terallethrin, prallethrin and transfluthrin, and plant essential oils having mothproofing effects such as nutmeg oil, clove oil, sage oil, thyme oil, lavender oil, basil oil, hinoki oil, lemongrass oil, cassia oil, pimento oil and alpiniaspeclosa oil.

The method of impregnating the non-woven fabric with the oily substance volatile at room temperature or increased temperature is not specially limited, while there is generally employed a method in which the non-woven fabric is immersed in the oily substance and then compressed with a press to adjust its content to a predetermined impregnation amount or a method in which the oily substance is directly dropwise applied to the non-woven fabric with a syringe and its content is adjusted to a predetermined impregnation amount. It is sufficient to use the oily substance in such an impregnation amount that the non-woven fabric becomes substantially transparent when impregnated with the oily substance. The above amount can be properly set in an amount range which generally does not exceed the non-woven fabric space volume, depending upon the non-woven fabric space volume and the use of the indicator material I as an end product.

The indicator material I of the present invention can be obtained by impregnating the non-woven fabric, of which one surface is provided with the predetermined resin layer, with the oily substance volatile at room temperature or increased temperature as described above. The indicator material I may be used as it is. For preventing the contact of the oily substance volatile at room temperature or increased temperature to articles around it, however, it is generally preferred to place it in a container of plastic, paper or a metal before setting it in a desired place. In this case, it is preferred to provide part of the container with an aperture, etc., such that a change in the indicator material I can be observed from outside of the container, i.e., such that the resin layer which is observable from the non-woven fabric side can be observed for a color change.

For example, when the volatile oily substance is a mothproofing agent volatile at room temperature, the above indicator material I can be used by directly placing it in a drawer of a chest. When the volatile oily substance is a deodorant volatile at room temperature, the indicator material I can be used by directly placing it in a room, in a rest room, a hall, an automobile, a refrigerator, or the like. When the volatile oily substance is an aromatic agent volatile at room temperature, the indicator material I can be used by directly placing it in a room, a rest room, a hall, an automobile, or the like. When the volatile oily substance is an insecticide volatile at an increased temperature, the indicator material I can be used by combining it with heating means used in an electrical mosquito preventing device and placing the combination in a room.

In the indicator material I used as described above, the non-woven fabric impregnated with a sufficient amount of the oily substance is substantially transparent, and a color of the colored portion of the resin layer formed on one surface of the non-woven fabric can be clearly observed when it is observed from the non-woven fabric side. However, the dissipation of the oily substance in the non-woven fabric occurs in the side opposite to the resin layer side, and the non-woven fabric gradually becomes non-transparent because of the dissipation of the oily substance which occurs with the passage of time. And, the non-woven fabric finally comes into a non-transparent state. Therefore, the resin layer observed from the non-woven fabric side gradually shifts from a visible state to a state masked by the non-woven fabric due to the dissipation of the oily substance which occurs with the passage of time. With the above shifting, a color observable from the non-woven fabric side gradually alters from the color of colored portion of the resin layer to the color of the non-woven fabric itself. That is, the indicator material I gradually and continuously changes in color from the color of the colored portion of the resin layer to the color of the non-woven fabric itself in accordance with a change in the degree of dissipation of the oily substance volatile at room temperature or increased temperature with which the non-woven fabric is impregnated. Therefore, the degree of dissipation of the oily substance volatile at room temperature or increased temperature can be recognized at a glance by observing the above change in color.

Figure 6:
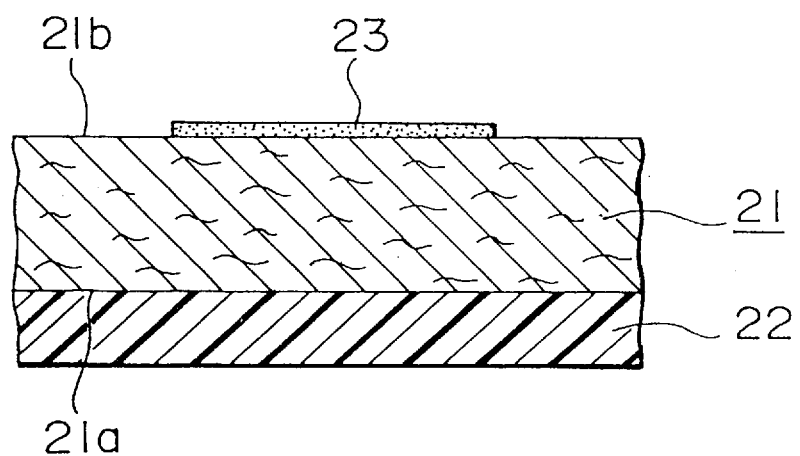
FIG. 6 is a schematic cross-sectional view of another preferred embodiment of an indicator material I.

Further, as shown in FIG. 6, when a print portion 23 of a character, a print, or the like showing the termination of dissipation (disappearance) of the oily substance (not shown) volatile at room temperature or increased temperature with which the non-woven fabric 21 is impregnated, in a similar color having a lower intensity than the colored portion of the resin layer 22, is provided, by a printing method, on a surface 21b opposite to a surface 21a of the non-woven fabric 21 on which the resin layer 22 is formed, the dissipation (disappearance) of the oily substance with which the non-woven fabric 21 is impregnated can be more effectively shown. The term "similar color having a lower intensity than the colored portion of the resin layer" refers to a color which is similar to, or has the same color tone as, that of the colored portion of the resin layer, but has a lower intensity than the same. In FIG. 6, members which appear in FIG. 5 are shown by the same reference numerals as those in FIG. 5.

The above print portion 23 may be of a character, a symbol, a painting or anything else. For example, the character may read "please replace", "termination of dissipation", "end", "END", etc., and the symbol may be "X", etc. The method of providing the above print portion 23 is not specially limited, and it is selected from a screen printing method, a gravure printing method, an offset printing method, a relief printing method and an inkjet printing method.

The print portion 23 is prepared so as to show a similar color having a lower intensity than the colored portion of the resin layer 22, and when the non-woven fabric 21 is transparent due to the impregnation with the oily substance, the print portion 23 is therefore similar to the color of colored portion of the resin layer 21 and is not decipherable even if the observation is made toward the resin layer 22 from the non-woven fabric 21 side. With the dissipation (disappearance) of the oily substance, the non-woven fabric 21 gradually becomes non-transparent, and the color of colored portion of the resin layer 22 decreases in intensity when observed. The print portion 23 provided on the non-woven fabric 21 accordingly gradually becomes decipherable, whereby the dissipation (disappearance) of the oily substance volatile at room temperature or increased temperature with which the non-woven fabric 21 is impregnated can be more effectively shown.

In the indicator material I, for effectively showing the degree of the oily substance volatile at room temperature or increased temperature with which the non-woven fabric is impregnated, preferably, the color of the non-woven fabric (color recognized when the non-woven fabric itself is observed, the term will be used in this sense hereinafter) is arranged to be white or similar to white, and the color of colored portion of the resin layer is arranged to be a deep color such as black, blue, red, green, violet, etc., as far as it is permitted. When the color of the non-woven fabric and the color of colored portion of the resin layer are selected as above, these colors have a high contrast, and the color change dependent upon the degree of dissipation of the oily substance volatile at room temperature or increased temperature becomes clearer.

The above-explained indicator material I works not only as a dissipation device which dissipates the oily substance volatile at room temperature or increased temperature with which the non-woven fabric is impregnated, but also as one having the indicator function to show the dissipation amount of the above oily substance. And, the non-woven fabric as a support works as a container for the oily substance volatile at room temperature or increased temperature.

Containing a fine-denier fiber having a size of 2 denier or less, the above non-woven fabric can support the oily substance more firmly and uniformly than a non-woven fabric which does not contain the fine-denier fiber. As a result, the oily substance with which the non-woven fabric is impregnated can be more uniformly dissipated. In the indicator material I, further, the resin layer gradually becomes masked by the non-woven fabric with the dissipation of the oily substance, and the above non-woven fabric is highly capable of masking the resin layer. In the indicator material I of the present invention, therefore, the site where to set it and the method of setting it are negligible, and further, the degree of dissipation of the oily substance which occurs with the passage of time can be clearly shown.

Further, containing a fine-denier fiber having a size of 2 denier or less, the above non-woven fabric is relatively highly capable of supporting the oily substance over a non-woven fabric which does not contain the fine-denier fiber, and the indicator material I of the present invention can therefore contain a relatively large amount of the oily substance.

The indicator material II of the present invention will be explained hereinafter.

The indicator material II of the present invention is the same as the above indicator material I except that the non-woven fabric which has a low refractive index and is used as a support has a partly altered density and that the non-woven fabric is not required to contain a fine-denier fiber having a size of 2 denier or less. Nevertheless, it is preferred to use a non-woven fabric containing a fine-denier fiber having a size of 2 denier or less for allowing the non-woven fabric to support the oily substance firmly and uniformly. Specific examples of the above non-woven fabric include those described in the explanation of the indicator material I.

The density of the non-woven fabric constituting the indicator material II partly altered, and the non-woven fabric therefore has a portion having a relatively high density and a portion having a relatively low density. In the non-woven fabric, the density of the "portion having a high density" (to be referred to as "high-density portion" hereinafter) is preferably 0.3 to 1.0 $g/cm^3$, and the density of the "portion having a low density" (to be referred to as "low-density portion" hereinafter) is preferably 0.1 to 0.5 $g/cm^3$. When the above density is lower than the 0.1 $g/cm^3$, undesirably, the non-woven fabric is poor in the capacity to support the volatile oily substance, and the oily substance may sag. When the above density is higher than 1.0 $g/cm^3$, there is no problem on the capacity to support the oily substance, while the showing function exhibited by the resin layer shifting from a visible state to a state masked by the non-woven fabric is no longer clear. The amount of the oily substance supported per unit area of the non-woven fabric is generally equivalent to, or smaller than, the non-woven fabric space volume of the non-woven fabric, and the space volume of the non-woven fabric used in the indicator material II is therefore preferably at least 50 $cm^3/m^3$, particularly preferably 50 to 1,800 $cm^3/m^3$ when the non-woven fabric is considered as a whole. The above range of the high-density portion and the above range of the low-density portion partly overlap, while the density of the former is naturally not higher than the density of the latter.

The high-density portion and the low-density portion can be disposed as required depending upon the use of the indicator material II as an end product. For example, the half of area of the non-woven fabric taken along the longitudinal direction or the transverse direction is arranged to be a high-density portion, and the remaining half is arranged to be a low-density portion. Further, the high-density portion and the low-density portion may be arranged such that they form the pattern of a lattice, a check, a honeycomb, a hexagon or concentric circles when the non-woven fabric is seen from the above. When the high-density portion and the low-density portion are disposed such that the high-density portion is surrounded by the low-density portion, the degree of dissipation of the oily substance can be more clearly shown. The reason therefore is assumed to be as follows.

The oily substance with which the non-woven fabric is impregnated dissipates from both the low-density portion and the high-density portion, while the oily substance present in the low-density portion spontaneously shifts into the high-density portion with the dissipation of the oily substance from the high-density portion. When the high-density portion is disposed such that part of the high-density portion is located in an edge portion of the non-woven fabric, the initial shifting of the oily substance from the low-density portion to the high-density portion with the dissipation of the oily substance is limited to the shifting of the oily substance from the low-density portion to that part of the high-density portion which is not located in the edge portion of the non-woven fabric. On the other hand, when the high-density portion and the low-density portion are disposed such that the high-density portion is surrounded by the low-density portion, the initial shifting of the oily substance from the low-density portion to the high-density portion with the dissipation of the oily substance takes place in all directions toward the high-density portion when viewed from the above. The shifting of the oily substance therefore takes place more effectively. Therefore, the oily substance remains in the high-density portion surrounded by the low-density portion even after the oily substance in the surrounding low-density portion has disappeared, and the degrees of color change with the dissipation of the oily substance therefore differ to a great extent between the high-density portion and the low-density portion when the indicator material II is observed from the non-woven fabric side. As a result, the degree of the oily substance can be more clearly shown.

The degree of process of the above color change in the high-density portion also depends upon to what extent the oily substance shifts from the low-density portion to the high-density portion. The degree of process of the above color change in the high-density portion therefore differs depending upon how the high-density portion is in contact to the low-density portion. Therefore, the time length required for the resin layer shifting from a visible state to a masked state in the high-density portion can be determined by adjusting how the high-density portion is in contact with the low-density portion when the high-density portion is formed.

The partly altered density of the non-woven fabric may be formed of two different density portions, a low-density portion and a high-density portion, may be formed of three different density portions, a low-density portion, an intermediate-density portion and a high-density portion, or may be formed of at least four different density portions.

The above non-woven fabric having a partly altered density can be obtained by preparing a non-woven fabric having a substantially uniform density by a dry method, a wet paper making method, or the like, and then partly roughening a desired portion on the surface of the non-woven fabric or pressing a desired portion of the non-woven fabric with a press roll, a hot press roll, an embossing roll, an embossing machine or the like. Further, the above non-woven fabric can be also obtained by combining non-woven fabrics having different densities. In the method of obtaining the non-woven fabric having a partly altered density by pressing a desired portion of a non-woven fabric, the processing is easy since a pressed portion alone has an increased density, and the form of a portion of which the density is desired to alter can be determined as required. The above method is therefore suitable as a method of partly altering the density of the non-woven fabric.

The basis weight of the "non-woven fabric having a partly altered density" differs depending upon the amount of the oily substance used for impregnating the non-woven fabric, while it is generally preferably 20 to 200 $g/m^2$.

In the indicator material II, a partly or wholly colored resin layer is formed on one surface of the above non-woven fabric. The material for the resin layer and the method of the formation thereof are the same as those explained with regard to the indicator material I, and their explanations are omitted here.

Like the oily substance used in the already described indicator material I, the oily substance volatile at room temperature or increased temperature used for impregnating the above non-woven fabric provided with the resin layer is selected, for example, from an oily aromatic, oily deodorants, oily mothproofing agents, oily insecticides, and the like, which are volatile at room temperature or increased temperature, depending upon use of the indicator material II as an end product. Specific examples of the above oily substance include those specified with regard to the already explained indicator material I of the present invention. Further, concerning the method of impregnating the non-woven fabric with the oily substance, the method shown in the explanation of the indicator material I of the present invention can be applied thereto.

The indicator material II of the present invention can be obtained by impregnating the non-woven fabric having one surface provided with the resin layer with oily substance volatile at room temperature or increased temperature. The indicator material II may be used as it is. As described with regard to the indicator material I, however, it is preferred to place it in a container of plastic, paper or a metal before setting it in a desired place. In this case, it is preferred to provide part of the container with an aperture, etc., such that a change in the indicator material IL can be observed from outside of the container, i.e., such that the resin layer which is observable from the non-woven fabric side can be observed for a color change. Like the indicator material I, the indicator material II is used by placing it in a desired place depending upon the kind of the oily substance used for impregnating the non-woven fabric.

In the indicator material II used as described above, the non-woven fabric impregnated with a sufficient amount of the oily substance is substantially transparent, and a color of the colored portion of the resin layer formed on one surface of the non-woven fabric can be clearly observed when it is observed from the non-woven fabric side. However, the dissipation of the oily substance in the non-woven fabric occurs in the side opposite to the resin layer side, and the non-woven fabric gradually becomes non-transparent because of the dissipation of the oily substance which occurs with the passage of time. And, the non-woven fabric finally comes into a non-transparent state. Therefore, the resin layer observed from the non-woven fabric side gradually shifts from a visible state to a state masked by the non-woven fabric due to the dissipation of the oily substance which occurs with the passage of time. With the above shifting, a color observable from the non-woven fabric side gradually alters from the color of colored portion of the resin layer to the color of the non-woven fabric itself. And, the above color change proceeds at a higher rate in the low-density portion than in the high-density portion of the non-woven fabric. The color change in the high-density portion and the color change in the low-density portion can be compared for confirmation, whereby the degree of dissipation of the oily substance can be more clearly recognized.

In the indicator material II of the present invention, for more clearly showing the dissipation (disappearance) of the oily substance with which the non-woven fabric is impregnated, a print portion showing the termination of dissipation of the oily substance may be prepared in a similar color having a lower intensity than the colored portion of the resin layer, and provided on a surface which is opposite to the surface of the non-woven fabric provided with the resin layer and has a high density in the non-woven fabric (the above print portion will be referred to as "print portion i" hereinafter). The print portion i may be of a character, a symbol, a painting or anything else. For example, the character may read "please replace", "termination of dissipation", "end", "END", etc., and the symbol may be "X", etc.

Further, a print portion showing that the oily substance is being dissipated, in a color which is similar to that of the colored portion of the resin layer but has a higher or equivalent intensity or is the same as that of the non-woven fabric, may be provided on a surface which is opposite to the surface of the non-woven fabric provided with the resin layer and has a low density in the non-woven fabric (the above print portion will be referred to as "print portion ii" hereinafter). The print portion ii may be of a character, a symbol, a painting or anything else. For example, the character may read "in use", "dissipating", "working", etc., and the symbol may be "→→→", etc.

The print portion ii of a symbol such as "→→→", "↑↑↑↑" or the like, a desired character or a painting may be provided in a color which is similar to that of the non-woven fabric such that the print portion ii is present in each of the low-density portion and the high-density portion or that the print portion ii bridges the low-density portion and the high-density portion.

The method of providing the above print portions i and ii maybe any method without any special limitation. There may be employed a screen printing method, a gravure printing method, an offset printing method, a relief printing method, an inkjet printing method or the like.

When the above print portion i is formed on the surface of the high-density portion of the non-woven fabric, the print portion i is similar to the color of colored portion of the resin layer and is not visually recognizable, since the non-woven fabric is substantially transparent at a time when the non-woven fabric is impregnated with the oily substance. With the dissipation (disappearance) of the oily substance, the non-woven fabric becomes gradually non-transparent so that the intensity of the color of the colored portion of the resin layer decreases, and the print portion i becomes decipherable. As a result, the degree of dissipation of the oily substance can be more finely shown.

When the above print portion i is formed on the surface of the high-density portion of the non-woven fabric and when the above print portion ii is provided in a color which has an intensity higher than, or equivalent to, the color of colored portion of the resin layer and is the same color as that of the colored portion, stepwise showing states like the following first to final steps can be achieved.

That is, in a first step, the non-woven fabric is substantially transparent, and the whole surface of the indicator material therefore shows the color of colored portion of the resin layer when the observation is made toward the resin layer side from the non-woven fabric side, so that it is confirmed that the non-woven fabric is impregnated with the oily substance.

A second step is there for a certain period of time after the initiation of use. In the second step, the color change with the dissipation of the oily substance proceeds at a higher rate in the low-density portion than in the high-density portion, and the print portion ii begins to appear. However, when the color of the print portion ii is the same color as that of the colored portion of the resin layer and has an intensity equivalent to that of the colored portion, the print portion ii is not yet visually recognizable. On the other hand, in a portion where the color change proceeds at a lower rate (high-density portion of the non-woven fabric), no change is visually recognizable, and this portion shows the color of colored portion of the resin layer.

In a subsequent third step, the color change with the dissipation of the oily substance further proceeds, and the low-density portion of the non-woven fabric becomes visually recognizable in a color of which the intensity is lower than that of the colored portion of the resin layer. As a result, the print portion ii comes into a state where the print portion ii is decipherable even if the print portion ii has the same color as that of the colored portion of the resin layer and has an intensity equivalent to that of the colored portion. In a portion where the color change proceeds at a lower rate (high-density portion of the non-woven fabric), however, the change is not yet visually recognizable.

In a subsequent fourth step, the color change with dissipation of the oily substance further proceeds, and the low-density portion of the non-woven fabric comes to show the original color of the non-woven fabric itself. In this portion, the resin layer is masked by the non-woven fabric, and the print portion ii is therefore clearly shown. On the other hand, in the portion where the color change proceeds at a lower rate (high-density portion of the non-woven fabric), the color changes to a low-intensity color. Since, however, the print portion i is also formed of a low-intensity color, the print portion i showing the end of dissipation is not yet visually recognizable.

In a final step, all of the oily substance used for the impregnation of the non-woven fabric are dissipated, both the portion where the color change proceeds at a higher rate (low-density portion of the non-woven fabric) and the portion where the color change proceeds at a lower rate (high-density portion of the non-woven fabric) show the color of the non-woven fabric itself, and the resin layer is masked by the non-woven fabric. Therefore, not only the print portion ii but also the print portion i are clearly shown. That is, the end of dissipation of the oily substance is clearly shown.

Further, when the print portion i is formed on the surface of the high-density portion of the non-woven fabric and when the print portion ii in the same color as that of the non-woven fabric is formed on the surface of the low-density portion of the non-woven fabric, stepwise showing states like the following first to final steps can be achieved.

That is, in a first step, the non-woven fabric is substantially transparent, and the print portion ii is formed in the same color as that of the non-woven fabric itself. Therefore, when the observation is made toward the resin layer from the non-woven fabric side, the print portion ii is clearly visually recognized, and the other portion shows the color of colored portion of the resin layer. The portion other than the print portion ii shows the color of colored portion of the resin layer, and it can be therefore confirmed that the non-woven fabric is impregnated with the oily substance.

A second step is there for a certain period of time after the initiation of use. In the second step, the color change with the dissipation of the oily substance proceeds at a higher rate in the low-density portion of the non-woven fabric than in the high-density portion, while the print portion ii is still visually recognizable since the print portion ii is formed in the same color as that of the non-woven fabric itself. On the other hand, in the portion where the color change proceeds at a lower rate (high-density portion of the non-woven fabric), no change is recognizable, and this portion shows the color of colored portion of the resin layer.

In a subsequent third step, the color change with the dissipation of the oily substance further proceeds, and the color on the portion where the color change proceeds at a higher rate (low-density portion of the non-woven fabric) changes to a low-intensity color. It is therefore becomes difficult to recognize the print portion ii, while the print portion ii is still visually recognizable. On the other hand, in the portion where the color change proceeds at a lower rate (high-density portion of the non-woven fabric), the change is not yet recognizable.

In a subsequent fourth step, the color change with the dissipation of the oily substance further proceeds, and the low-density portion of the non-woven fabric comes to show the original color of the non-woven fabric itself. Therefore, the print portion ii formed in the same color as that of the non-woven fabric itself becomes visually unrecognizable. On the other hand, the portion where the color change proceeds at a lower rate (high-density portion of the non-woven fabric) is altered to a low-intensity color. Since, however, the print portion i is formed in a similar color having a lower intensity than the colored portion of the resin layer, the print portion i is not visually recognizable in this state.

In a final step, all of the oily substance used for the impregnation of the non-woven fabric is dissipated, and both of the portion where the color change proceeds at a higher rate (low-density portion of the non-woven fabric) and the portion where the color change proceeds at a lower rate (high-density portion) come to show the color of the non-woven fabric itself. Therefore, the print portion ii formed in the color similar to the color of the non-woven fabric itself is not visually recognizable as is not in the fourth step, while the print portion i formed in the similar color having a lower intensity than the colored portion of the resin layer is clearly shown. That is, the end of dissipation of the oily substance is clearly shown.

Further, when the print portion ii of a symbol such as "→→→", "↑↑↑↑" or the like, a desired character or a painting may be provided in a color which is similar to that of the non-woven fabric such that the print portion ii is present in each of the low-density portion and the high-density portion or that the print portion ii bridges the low-density portion and the high-density portion, stepwise showing states like the following first to final steps can be achieved.

That is, in a first step, the non-woven fabric is substantially transparent, and the print portion ii is formed in the same color as that of the non-woven fabric. When the observation is made toward the resin layer side from the non-woven fabric side, the print portion ii as a whole is clearly visually recognized, and the other portion shows the color of colored portion of the resin layer. Since the portion other than the print portion ii shows the color of colored portion of the resin layer, it is confirmed that the non-woven fabric is impregnated with the oily substance.

A second step is there for a certain period of time after the initiation of use. In the second step, the color change with the dissipation of the oily substance proceeds at a higher rate in the low-density portion of the non-woven fabric than in the high-density portion, while the print portion ii as a whole is still visually recognizable since the print portion ii is formed in the same color as that of the non-woven fabric itself.

In a subsequent third step, the color change with the dissipation of the oily substance further proceeds, and the color of the portion where the color change proceeds at a higher rate (low-density portion of the non-woven fabric) therefore alters to a low-intensity color, so that it becomes difficult to visually recognize the print portion ii on that portion. However, the print portion ii on that portion is still recognizable. On the other hand, the print portion ii on the portion where the color change proceeds at a lower rate (high-density portion of the non-woven fabric) is still clearly visually recognizable.

In a subsequent fourth step, the color change with the dissipation of the oily substance further proceeds, and the low-density portion of the non-woven fabric comes to show the original color of the non-woven fabric itself. Therefore, that portion of the print portion ii which is formed on the portion where the color change proceeds at a higher rate (low-density portion of the non-woven fabric) becomes visually unrecognizable. On the other hand, the portion where the color change proceeds at a lower rate (high-density portion of the non-woven fabric) alters to a low-intensity color, while the print portion ii on the above portion is still visually recognizable since the print portion ii is formed in the same color as that of the non-woven fabric.

In a final step, all of the oily substance used for the impregnation of the non-woven fabric is dissipated, and both of the portion where the color change proceeds at a higher rate (low-density portion of the non-woven fabric) and the portion where the color change proceeds at a lower rate (high-density portion) come to show the color of the non-woven fabric itself. Therefore, the print portion ii formed in the color similar to the color of the non-woven fabric itself is not visually recognizable. That is, the end of dissipation of the oily substance is clearly shown.

In the indicator material II as well as the indicator material I, for effectively showing the degree of the oily substance volatile at room temperature or increased temperature with which the non-woven fabric is impregnated, preferably, the color of the non-woven fabric (color of the non-woven fabric before it is impregnated with the oily substance) is arranged to be white or similar to white, and the color of the resin layer is arranged to be a deep color such as black, red, green, violet, etc., as far as it is permitted. When the color of the non-woven fabric and the color of colored portion of the resin layer are selected as above, these colors have a high contrast, and the color change dependent upon the degree of dissipation of the oily substance volatile at room temperature or increased temperature becomes clearer.

The above-explained indicator material II works not only as a dissipation device which dissipates the oily substance volatile at room temperature or increased temperature with which the non-woven fabric is impregnated, but also as one having the indicator function to show the dissipation amount of the above oily substance. And, the non-woven fabric as a support works as a container for the oily substance volatile at room temperature or increased temperature.

Having partly altered density, the above non-woven fabric has a portion where the color change with the dissipation of the oily substance which occurs with the passage of time proceeds at a higher rate (low-density portion) and a portion where the above color change proceeds at a lower rate (high-density portion). The indicator material II can therefore can clearly show not only a time of expiration of the oily substance but also the degree of dissipation of the oily substance which occurs with the passage of time, based on a difference between the color change in the portion where the color change with the dissipation of the oily substance which occurs with the passage of time proceeds at a higher rate (low-density portion) and the portion where the above color change proceeds at a lower rate (high-density portion). Further, the color change in the above portion where the color change proceeds at a higher rate and the color change in the above portion where the color change proceeds at a lower rate take place independently of each other substantially regardless of a place where the indicator material II is set and the method of setting it. The indicator material II can be therefore set in any site and by any method so long as it is in a state where the observation can be made toward the resin layer side from the non-woven fabric side.

When a non-woven fabric containing a fine-denier fiber having a size of 2 denier or less is used as the above non-woven fabric, not only the oily substance used for the impregnation of the non-woven fabric can be more uniformly dissipated, but also the capability of masking the resin layer with the non-woven fabric is improved, similarly to the indicator material I. The indicator material II can therefore more clearly show not only a time of expiration of the oily substance but also the degree of dissipation of the oily substance which occurs with the passage of time. At the same time, the capacity of the non-woven fabric to support the oily substance relatively improves, and the indicator material II can therefore contain a relatively large amount of the oily substance.

The present invention will be explained more in detail with reference to Examples hereinafter, while the content of the present invention shall not be limited to the following Examples, in which "part" stands for "part by weight".

EXAMPLES 1–13

(Preparation of indicator material I) and Comparative Examples 1–2

Fabrics were prepared from fibers shown in Table 1 or 2 in amounts shown in Table 1 or 2 by a wet paper making method using a cylinder paper machine, and then a wet press part, a dry part and a calender part were properly adjusted in each of Examples and Comparative Examples to prepare non-woven fabrics as a support. In Example 13 alone, however, the non-woven fabric was prepared by a dry method (carding method). These non-woven fabrics showed white as original color, and all the non-woven fabrics had a refractive index of 1.7 or less. Table 1 or 2 shows the basis weights, densities and non-woven fabric space volumes of the so-obtained non-woven fabrics.

A resin composition prepared by incorporating 1% of Blue Ultramarine into a low-density polyethylene (NUC8008, supplied by Nippon Unicar) was applied to one surface of each of the above non-woven fabrics by melt extrusion at a resin temperature of 320° C. to form a resin layer of which the entire surface was colored in deep blue. In the application by melt extrusion, a melt extrusion application machine was used, and the application amount of the resin was set at 20 g/m$^2$.

The above non-woven fabrics each of which had one surface on which the resin layer was formed, were receptively impregnated with 100 g/m$^2$ of isobutyl acetate, whereby indicator materials I included in the present invention were obtained in Examples 1 to 13, and indicator materials not included in the present invention were obtained in Comparative Examples 1 and 2.

Among the above indicator materials, all the indicator materials I included in the present invention could clearly show the degree of dissipation of the oily substance (isobutyl acetate) with the passage of time even if they were set horizontally, set slantly or suspended vertically. These data show that these indicator materials I can be used regardless of a setting site and a setting method. The indicator materials obtained in Examples 1 to 13 and Comparative Examples 1 and 2 were determined or evaluated for performances by the following methods.

[Visibility of resin layer]

When the indicator materials I were observed from the non-woven fabric side to the resin layer side, it was determined how clearly the color of the resin layer could be visually recognized.

A: The color of the resin layer could be clearly recognized.

B: The indicator material had an intermediate performance between A and C.

C: The color of the resin layer was whitish to some extent, but could be recognized.

D: The indicator material had an intermediate performance between C and E (different from E in which the indicator material could not be put to use).

E: No color of the resin layer could be recognized.

[Capability of masking resin layer]

When the indicator materials I were observed from the non-woven fabric side to the resin layer side at a time when the oily substance was completely dissipated by allowing the indicator materials I to stand at room temperature, the capability of masking the resin layer with the non-woven fabric was determined.

A: The masking capability of the non-woven fabric was perfect so that no color of the resin layer could be recognized.

B: The indicator material had an intermediate performance between A and C.

C: The masking capability of the non-woven fabric was imperfect to some extent, and the color of the resin layer could be recognized to some extent.

D: The indicator material had an intermediate performance between C and E (different from E in which the indicator material could not be put to use).

E: The masking capability of the non-woven fabric was imperfect, and the color of the resin layer could be recognized.

[Capability of shifting in showing]

The indicator materials I were allowed to stand at room temperature, and color changes with the passage of time when the indicator materials were observed from the non-woven fabric side to the resin layer side were evaluated.

A: The indicator material showed a clear color change.

B: The indicator material had an intermediate performance between A and C.

C: The indicator material showed a color change although it was unclear to some extent.

D: The indicator material had an intermediate performance between C and E (different from E in which the indicator material could not be put to use).

E: The indicator material showed almost no color change.

[Capacity to support oily substance]

The indicator materials I were perpendicularly suspended, and a degree to which the oily substance was held in the indicator material was determined.

A: No oily substance leaked from the indicator material.

B: The indicator material had an intermediate performance between A and C.

C: A puddle of the oily substance was formed below the indicator material.

D: The indicator material had an intermediate performance between C and E (different from E in which the indicator material could not be put to use).

E: The oily substance leaked from the indicator material.

TABLE 1

| | Fibers and their amounts for non-woven fabric | Basis weight g/m² | Density g/cm³ | Space volume cm³/m² |
|---|---|---|---|---|
| Example 1 | Acrylic fiber (supplied by Mitsubishi Rayon Co., Ltd.) 0.1 d *1, 3 mm, 50 parts Heat-fusible fiber (NBF-E, supplied by Daiwabo) 2d, 5 mm, 50 parts | 50 | 0.25 | 151.9 |
| Example 2 | Acrylic fiber (supplied by Mitsubishi Rayon Co., Ltd.) 0.5 d, 3 mm, 50 parts Heat-fusible fiber (NBF-E, supplied by Daiwabo) 2d, 5 mm, 50 parts | 50 | 0.22 | 179.2 |
| Example 3 | Acrylic fiber (supplied by Mitsubishi Rayon Co., Ltd.) 1.5 d, 3 mm, 50 parts Heat-fusible fiber (NBF-E, supplied by Daiwabo) 2d, 5 mm, 50 parts | 50 | 0.21 | 190.0 |
| Example 4 | Acrylic fiber (supplied by Mitsubishi Rayon Co., Ltd.) 2 d, 3 mm, 50 parts Heat-fusible fiber (NBF-E, supplied by Daiwabo) 2d, 5 mm, 50 parts | 50 | 0.20 | 201.9 |
| Example 5 | Acrylic fiber (supplied by Mitsubishi Rayon Co., Ltd.) 1.0 d, 3 mm, 50 parts Heat-fusible fiber (NBF-E, supplied by Daiwabo) 3d, 5 mm, 50 parts | 45 | 0.20 | 181.7 |
| Example 6 | Polyester fiber -B*2 (supplied by Kuraray Co., Ltd.) 1.3 d, 5 mm, 50 parts Heat-fusible fiber (NBF-E, supplied by Daiwabo) 2d, 5 mm, 50 parts | 45 | 0.20 | 186.0 |
| Example 7 | Polyester fiber-SD*3 (supplied by Teijin Ltd.) 1.5 d, 5 mm, 50 parts Heat-fusible fiber (NBF-E, supplied by Daiwabo) 2d, 5 mm, 50 parts | 45 | 0.20 | 186.0 |
| Example 8 | Acrylic fiber (supplied by Mitsubishi Rayon Co., Ltd.) 0.5 d, 3 mm, 40 parts Heat-fusible fiber (NBF-E, supplied by Daiwabo) 3d, 5 mm, 30 parts Natural pulp (LBKP) 30 parts | 50 | 0.28 | 135.0 |

*1: d stands for denier.
*2: B stands for "bright" and means that a fiber contains no, or very small amount of, white pigment. The color of the fiber is transparent.
*3: SD stands for semi-double and means that a fiber contains a white pigment. The color of the fiber is white.

TABLE 2

| | Fibers and their amounts for non-woven fabric | Basis weight g/m² | Density g/cm³ | Space volume cm³/m² |
|---|---|---|---|---|
| Example 9 | Acrylic fiber (supplied by Mitsubishi Rayon Co., Ltd.) 1.0 d, 3 mm, 9 parts Acrylic fiber (supplied by Mitsubishi Rayon Co., Ltd.) 3.0 d, 3 mm, 41 parts Heat-fusible fiber (NBF-E, supplied by Daiwabo) 3d, 5 mm, 50 parts | 40 | 0.15 | 228.2 |
| Example 10 | Acrylic fiber (supplied by Mitsubishi Rayon Co., Ltd.) 1.0 d, 3 mm, 20 parts Acrylic fiber (supplied by Mitsubishi Rayon Co., Ltd.) 3.0 d, 3 mm, 30 parts Heat-fusible fiber (NBF-E, supplied by Daiwabo) 3d, 5 mm, 50 parts | 40 | 0.18 | 183.8 |
| Example 11 | Acrylic fiber (supplied by Mitsubishi Rayon Co., Ltd.) 1.0 d, 3 mm 5 parts Acrylic fiber (supplied by Mitsubishi Rayon Co., Ltd.) 3.0 d, 3 mm, 45 parts Heat-fusible fiber (NBF-E, supplied by Daiwabo) 3d, 5 mm, 50 parts | 40 | 0.14 | 247.3 |
| Example 12 | Acrylic fiber (supplied by Mitsubishi Rayon Co., Ltd.) 1.0 d, 3 mm, 50 parts Heat-fusible fiber (NBF-E, supplied by Daiwabo) 3d, 5 mm, 50 parts | 30 | 0.09 | 304.5 |
| Example 13 | Polyester fiber -B (supplied by Kuraray Co., Ltd.) 2 d, 51 mm, 50 parts Heat-fusible fiber (NBF-E, supplied by Daiwabo) 2d, 51 mm, 50 parts Produced by dry method (carding method) | 40 | 0.10 | 365.4 |
| Comparative Example 1 | Acrylic fiber (supplied by Mitsubishi Rayon Co., Ltd.) 3.0 d, 3 mm, 80 parts Heat-fusible fiber (NBF-E, supplied by Daiwabo) 3d, 5 mm, 20 parts | 40 | 0.15 | 228.2 |
| Comparative Example 2 | Polyester fiber -B (supplied by Kuraray Co., Ltd.) 3.0 d, 5 mm, 70 parts Heat-fusible fiber (NBF-E, supplied by Daiwabo) 3d, 5 mm, 30 parts | 40 | 0.15 | 232.2 |

Comparative Example 3

A non-woven fabric as a support was prepared from 50 parts of an acrylic fiber (supplied by Mitsubishi Rayon Co., Ltd., 0.1 d, 3 mm) and 50 parts of a heat-fusible fiber (NBF-E, supplied by Daiwabo, 2 d, 5 mm) by a wet paper making method using a cylinder paper machine. The prepared non-woven fabric had a basis weight of 50 g/m and a density of 0.33 g/cm³. No resin layer was formed.

Comparative Example 4

A resin composition prepared by incorporating 1% of Blue Ultramarine into a low-density polyethylene (NUC8008, supplied by Nippon Unicar) was applied by melt extrusion at a resin temperature of 320° C. to obtain a 50 g/m² film, which was used as a resin layer. No support of a non-woven fabric was formed.

The indicator materials of Examples 1 to 13 and Comparative Examples 1 and 2 shown in Table 1 or 2 and the indicator materials of Comparative Examples 3 and 4 were determined or evaluated for visibility of resin, capability of masking resin, capability of shifting in showing and capacity to support oily substance, and Table 3 shows the results. Those found in the determination or evaluation of the above characteristics are shown in the column of Remarks.

TABLE 3

|        | Visi-<br>bility of<br>resin<br>layer | Capa-<br>bility of<br>masking<br>resin<br>layer | Capa-<br>bility of<br>shifting<br>in<br>showing | Capacity<br>to hold<br>oily<br>substance | Remarks |
|--------|------|------|------|------|---------|
| Ex. 1  | A | A | A | A | — |
| Ex. 2  | A | A | A | A | — |
| Ex. 3  | A | B | A | B | — |
| Ex. 4  | A | C | A | C | — |
| Ex. 5  | A | B | A | B | — |
| Ex. 6  | A | B | A | B | — |
| Ex. 7  | C | B | C | B | — |
| Ex. 8  | C | A | C | A | — |
| Ex. 9  | A | C | C | C | — |
| Ex. 10 | A | B | B | B | — |
| Ex. 11 | A | D | D | D | — |
| Ex. 12 | A | C | C | D | — |
| Ex. 13 | A | C | D | D | As compared with non-woven fabric prepared by wet method, the formation was poor, and the evaluation varied. |
| CEx. 1 | A | D | D | E | — |
| CEx. 2 | A | D | D | E | — |
| CEx. 3 | E | E | E | A | Since no resin layer was formed, there was no color change. |
| CEx. 4 | E | E | E | E | Could not be impregnated with isobutyl acetate. |

Ex. = Example, CEx. = Comparative Example

EXAMPLE 14
(Preparation of indicator material I)

A non-woven fabric as a support was prepared in the same manner as in Example 1, and a resin layer was formed on one surface of the above non-woven fabric in the same manner as in Example 1 except that Blue Ultramarine was not incorporated into a low-density polyethylene (NUC8008, supplied by Nippon Unicar Co., Ltd.) or that the low-density polyethylene alone was used as a raw material for the resin layer. Then, printing was conducted on the surface of the above resin layer in indigo blue by an offset printing method using an indigo blue ink (TSP202 Blue, supplied by Toyo Ink Manufacturing Co., Ltd.).

Then, the above non-woven fabric was impregnated with isobutyl acetate in the same manner as in Example 1 to give an indicator material I.

The obtained indicator material I was determined or evaluated for performances in the same manner as in Example 1 to show that it could be set regardless of a setting site and a setting method and that it could clearly show the degree of dissipation of the oily substance (isobutyl acetate) with the passage of time.

EXAMPLE 15
(Preparation of indicator material I)

A non-woven fabric provided with a resin layer on one surface was prepared in the same manner as in Example 1, and then a print portion of "End" was formed on a surface opposite to the resin layer, i.e., on the non-woven fabric surface by an offset printing method using a tinting shade blue ink (TSP202 Blue, supplied by Toyo Ink Manufacturing Co., Ltd.) which was a similar color having a lower intensity than the color of the resin layer.

Then, the non-woven fabric was impregnated with isobutyl acetate in the same manner as in Example 1 to give an indicator material I.

Immediately after the above indicator material was prepared, the characters of "End" were not recognizable. However, with the dissipation of the isobutyl acetate, the characters of "End" gradually became recognizable, and when the isobutyl acetate was completely dissipated (disappeared), the characters of "End" could be clearly deciphered. As a result, the expiration of the isobutyl acetate could be more clearly recognized.

The above indicator material I could be set regardless of a setting site and a setting method similarly to the indicator material I obtained in Example 1, and the indicator material I could clearly show the degree of dissipation of the oily substance (isobutyl acetate) which occurred with the passage of time.

EXAMPLE 16
(Preparation of indicator material I)

A non-woven fabric provided with a resin layer on one surface was prepared in the same manner as in Example 1, and then a print portion of "Dissipating" was formed on a surface opposite to the resin layer, i.e., on the non-woven fabric surface by an offset printing method using a white ink (TSP202 White, supplied by Toyo Ink Manufacturing Co., Ltd.) which was a color similar to the color of the non-woven fabric.

Then, the non-woven fabric was impregnated with isobutyl acetate in the same manner as in Example 1, to give an indicator material I.

Immediately after the above indicator material I was prepared, the characters of "Dissipating" were clearly decipherable against deep blue which was the color of the resin layer. With the dissipation of the isobutyl acetate, the deciphering of the characters of "Dissipating" gradually became difficult, and when the isobutyl acetate was completely dissipated (disappeared), the characters of "Dissipating" were not at all decipherable. In the above indicator material I, the dissipation state of the isobutyl acetate could be more clearly recognized as described above.

The above indicator material I could be set regardless of a setting site and a setting method similarly to the indicator material I obtained in Example 1, and the indicator material I could clearly show the degree of dissipation of the oily substance (isobutyl acetate) which occurred with the passage of time.

EXAMPLES 17–29
(Preparation of indicator material I) and Comparative Examples 5–8

Fabrics were prepared from fibers shown in Table 4, 5 or 6 amounts shown in Table 4, 5 or 6 by a wet paper making method using a cylinder paper machine, and then a wet press part, a dry part and a calender part were properly adjusted in each of Examples and Comparative Examples to prepare non-woven fabrics as a support. In Example 27 alone, however, the non-woven fabric was prepared by a dry method. Table 4, 5 or 6 shows the basis weights, the non-woven fabric densities, the fiber densities and the non-woven fabric space volumes of these prepared non-woven fabrics. These non-woven fabrics showed white as original color, and all the non-woven fabrics had a refractive index of 1.7 or less.

A resin layer was formed on one surface of each of the above non-woven fabrics in the same manner as in Example 1. Further, in Example 28, characters of "Please replace" (showing of end of dissipation) as a print portion showing the end of dissipation were offset-printed on the surface portion of the non-woven fabric, i.e., a surface on which the resin layer was not formed, in a tinting shade blue color having a lower intensity than the resin layer. Further, in Example 29, not only the same print portion as that in Example 28 was formed, but also characters of "Dissipating" (showing of the dissipation occurring) as a print portion showing the dissipation occurring were printed on in a white color which was the same as the original color of the non-woven fabric.

Then, each non-woven fabric was impregnated with empenthrin which is a liquid mothproofing agent (oily mothproofing agent volatile at room temperature) in an amount ($cm^3/m^2$) equivalent to the non-woven fabric space volume of each, whereby indicator materials I included in the present invention were obtained in Examples 17 to 29 and indicator materials not included in the present invention were obtained in Comparative Examples 5 to 8. These indicator materials were determined or evaluated for performances in the same manner as in Example 1.

TABLE 4

| | Fibers and their amounts for non-woven fabric | Basis weight $g/m^2$ | Density of non-woven fabric $g/cm^3$ | Density of fiber $g/cm^3$ | Non-woven fabric space volume $(cm^3/m^2)$ |
|---|---|---|---|---|---|
| Ex. 17 | Acrylic fiber (supplied by Mitsubishi Rayon Co., Ltd.) 0.1 d *1, 3 mm, 50 parts | 50 | 0.25 | 1.15 | 151.9 |
| | Heat-fusible fiber (NBF-E, supplied by Daiwabo) 2d, 5 mm, 50 parts | | | 0.93 | |
| Ex. 18 | Acrylic fiber (supplied by Mitsubishi Rayon Co., Ltd.) 0.5 d, 3 mm, 50 parts | 50 | 0.22 | 1.15 | 179.2 |
| | Heat-fusible fiber (NBF-E, supplied by Daiwabo) 2.0 d, 5 mm, 50 parts | | | 0.93 | |
| Ex. 19 | Acrylic fiber (supplied by Mitsubishi Rayon Co., Ltd.) 1.0 d, 3 mm, 50 parts | 45 | 0.20 | 1.15 | 181.7 |
| | Heat-fusible fiber (NBF-E, supplied by Daiwabo) 3.0 d, 5 mm, 50 parts | | | 0.93 | |
| Ex. 20 | Polyester fiber -B*2 (supplied by Kuraray Co., Ltd.) 1.3 d, 5 mm, 50 parts | 45 | 0.20 | 1.38 | 186.0 |
| | Heat-fusible fiber (NBF-E, supplied by Daiwabo) 2.0 d, 5 mm, 50 parts | | | 0.93 | |
| Ex. 21 | Acrylic fiber (supplied by Mitsubishi Rayon Co., Ltd.) 0.1 d, 3 mm, 70 parts | 45 | 0.50 | 1.15 | 48.1 |
| | Heat-fusible fiber (NBF-E, supplied by Daiwabo) 2.0 d, 5 mm, 30 parts | | | 0.93 | |
| Ex. 18 | Acrylic fiber (supplied by Mitsubishi Rayon Co., Ltd.) 0.1 d, 3 mm, 60 parts | 50 | 0.40 | 1.15 | 77.4 |
| | Heat-fusible fiber (NBF-E, supplied by Daiwabo) 2.0 d, 5 mm, 40 parts | | | 0.93 | |

Ex. = Example
*1: The same meaning as that in note to Table 1.
*2: The same meaning as that in note to Table 1.

TABLE 5

| | Fibers and their amounts for non-woven fabric | Basis weight $g/m^2$ | Density of non-woven fabric $g/cm^3$ | Density of fiber $g/cm^3$ | Non-woven fabric space volume $(cm^3/m^2)$ |
|---|---|---|---|---|---|
| Ex. 23 | Polyester fiber-SD*3 (supplied by Teijin Ltd.) 1.5 d, 5 mm, 50 parts | 45 | 0.20 | 1.38 | 186.0 |
| | Heat-fusible fiber (NBF-E, supplied by Daiwabo) 2.0 d, 5 mm, 50 parts | | | 0.93 | |
| Ex. 24 | Acrylic fiber (supplied by Mitsubishi Rayon Co., Ltd.) 0.5 d, 3 mm, 40 parts | 50 | 0.28 | 1.15 | 135.0 |
| | Heat-fusible fiber (NBF-E, supplied by Daiwabo) 3.0 d, 5 mm, 30 parts | | | 0.93 | |
| | Natural pulp (LBKP) 30 parts | | | 1.50 | |
| Ex. 25 | Acrylic fiber (supplied by Mitsubishi Rayon Co., Ltd.) 1.0 d, 3 mm, 9 parts | 40 | 0.15 | 1.15 | 228.2 |
| | Acrylic fiber (supplied by Mitsubishi Rayon Co., Ltd.) 3.0 d, 3 mm, 41 parts | | | 1.15 | |
| | Heat-fusible fiber (NBF-E, supplied by Daiwabo) 3.0 d, 5 mm, 50 parts | | | 0.93 | |
| Ex. 26 | Acrylic fiber (supplied by Mitsubishi Rayon Co., Ltd.) 1.0 d, 3 mm, 50 parts | 30 | 0.09 | 1.15 | 304.5 |
| | Heat-fusible fiber (NBF-E, supplied by Daiwabo) 3.0 d, 5 mm, 50 parts | | | 0.93 | |
| Ex. 27 | Polyester fiber -B*2 (supplied by Kuraray Co., Ltd.) 2.0 d, 51 mm, 50 parts | 40 | 0.10 | 1.38 | 365.4 |
| | Heat-fusible fiber (NBF-E, supplied by Daiwabo) 2.0 d, 51 mm, 50 parts *Produced by dry method. | | | 0.93 | |

Ex. = Example
*3: The same meaning as that in note to Table 1.
*2: The same meaning as that in note to Table 1.

TABLE 6

| | Fibers and their amounts for non-woven fabric | Basis weight g/m² | Density of non-woven fabric g/cm³ | Density of fiber g/cm³ | Non-woven fabric space volume (cm³/m²) |
|---|---|---|---|---|---|
| Ex. 28 | Acrylic fiber (supplied by Mitsubishi Rayon Co., Ltd.) 0.5 d, 3 mm, 50 parts | 50 | 0.30 | 1.15 | 118.6 |
| | Heat-fusible fiber (NBF-E, supplied by Daiwabo) 3.0 d, 5 mm, 50 parts | | | 0.93 | |
| Ex. 29 | Acrylic fiber (supplied by Mitsubishi Rayon Co., Ltd.) 0.5 d, 3 mm, 50 parts | 50 | 0.30 | 1.15 | 118.6 |
| | Heat-fusible fiber (NBF-E, supplied by Daiwabo) 3.0 d, 5 mm, 50 parts | | | 0.93 | |
| CEx. 5 | Acrylic fiber (supplied by Mitsubishi Rayon Co., Ltd.) 3.0 d, 3 mm, 80 parts | 40 | 0.15 | 1.15 | 228.2 |
| | Heat-fusible fiber (NBF-E, supplied by Daiwabo) 3.0 d, 5 mm, 20 parts | | | 0.93 | |
| CEx. 6 | Polyester fiber -B*2 (supplied by Kuraray Co., Ltd.) 3.0 d, 5 mm, 70 parts | 40 | 0.15 | 1.38 | 232.0 |
| | Heat-fusible fiber (NBF-E, supplied by Daiwabo) 3.0 d, 5 mm, 30 parts | | | 0.93 | |
| CEx. 7 | Acrylic fiber (supplied by Mitsubishi Rayon Co., Ltd.) 0.1 d, 3 mm, 50 parts | 50 | 0.33 | 1.15 | 103.4 |
| | Heat-fusible fiber (NBF-E, supplied by Daiwabo) 2.0 d, 5 mm, 50 parts *No resin layer was formed. | | | 0.93 | |
| CEx. 8 | No support of non-woven fabric was provided, and a resin layer alone was used. The resin amount was adjusted to 50 g/m². | — | — | — | — |

Ex. = Example, CEx. = Comparative Example
*2: The same meaning as that in note to Table 1.

The indicator materials of Examples 17 to 29 and Comparative Examples 5 to 8 shown in Table 4, 5 or 6 were determined or evaluated for visibility of resin, capability of masking resin, capability of shifting in showing and capacity to support oily substance, and Table 7 shows the results. Those found in the determination or evaluation of the above characteristics are shown in the column of Remarks.

TABLE 7

| | Visibility of resin layer | Capability of masking resin layer | Capability of shifting in showing | Capacity to hold oily substance | Remarks |
|---|---|---|---|---|---|
| Ex. 17 | A | A | A | A | — |
| Ex. 18 | A | A | A | A | — |
| Ex. 19 | A | B | A | B | — |
| Ex. 20 | A | B | A | B | — |
| Ex. 21 | A | A | A | A | Shorter than a desired time length of dissipation |
| Ex. 22 | A | A | A | A | — |
| Ex. 23 | C | B | C | B | — |
| Ex. 24 | C | A | C | A | — |
| Ex. 25 | A | C | C | C | — |
| Ex. 26 | A | C | C | D | — |
| Ex. 27 | A | C | D | D | As compared with non-woven fabric prepared by wet method, the formation was poor, and the evaluation varied. |
| Ex. 28 | A | A | A | A | Showing of end of dissipation was confirmed by disappearance of empenthrin. |
| Ex. 29 | A | A | A | A | The end of dissipation was confirmed by disappearance of showing of dissipating based on the disappearance of empenthrin. |
| CEx. 5 | A | D | D | E | — |
| CEx. 6 | A | D | D | E | — |
| CEx. 7 | E | E | E | A | Since no resin layer was formed, there was no color change. |
| CEx. 8 | E | E | E | E | Could not be impregnated with empenthrin. |

The above indicator materials I obtained in Examples 17 to 29 could be set regardless of a setting site and a setting method similarly to the indicator material I obtained in Example 1, and these indicator materials I could clearly show the degree of dissipation of the oily substance (isobutyl acetate) which occurred with the passage of time.

EXAMPLE 30
(Preparation of indicator material II)

A non-woven fabric as a support was prepared from 50 parts by weight of an acrylic fiber (supplied by Mitsubishi Rayon Co., Ltd., 0.5 d, 3 mm) and 50 parts by weight of a heat-fusible fiber (NBF-E, supplied by Daiwabo, 3d, 5 mm) by a wet paper making method using a cylinder paper machine. The prepared non-woven fabric had a basis weight of 50 g/m² and a density of 0.3 g/cm³.

About a half of the surface of the above non-woven fabric was pressed with a press roll to increase the density of that portion, whereby a high-density portion and a low-density portion were formed in the non-woven fabric. The high-density portion formed by the above pressing had a density of 0.5 g/cm and the low-density portion (portion not pressed) had a density of 0.3 g/cm³. The non-woven fabric showed the original color of white.

Figure 1:
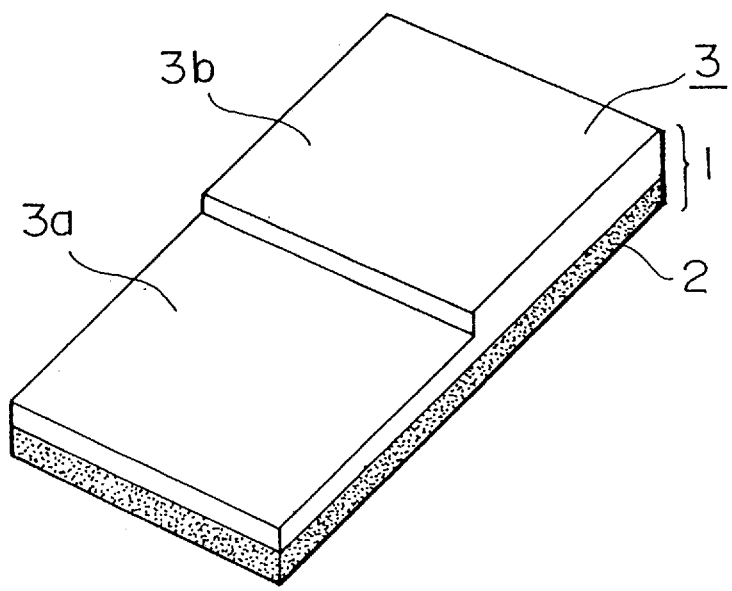
FIG. 1 is a schematic perspective view of a non-woven fabric-resin laminate prepared in Example 30.

A resin layer was formed on one surface of the above non-woven fabric in the same manner as in Example 1. FIG. 1 shows a perspective view of a non-woven fabric-resin laminate 1 obtained above. In said Figure, the non-woven fabric-resin laminate 1 was formed of the resin layer 2 and the non-woven fabric 3, and the non-woven fabric 3 had the high-density portion 3a and the low-density portion 3b.

Figure 2:
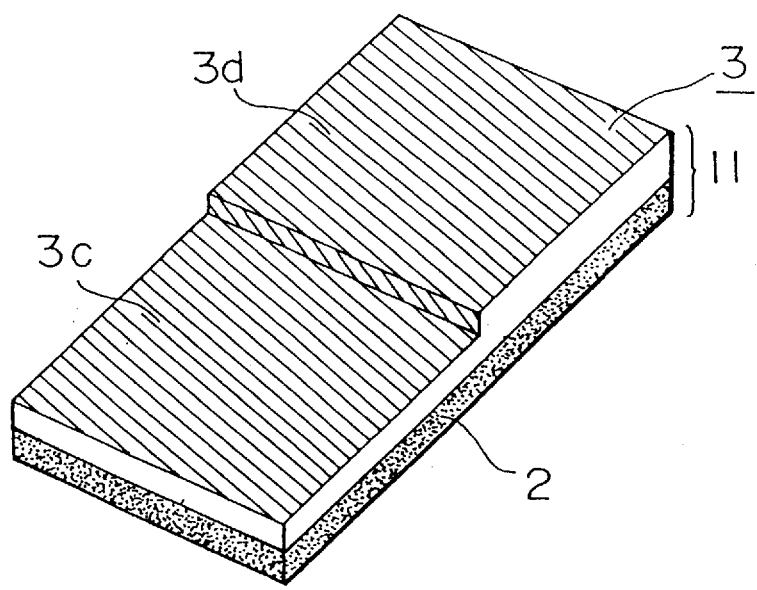
FIG. 2 is a schematic perspective view of an indicator material II prepared in Example 30.

The non-woven fabric 3 of the above-prepared non-woven fabric-resin laminate 1 was impregnated with isobutyl acetate in the same manner as in Example 1 to give an indicator material II. FIG. 2 shows a perspective view of the indicator material II. In the indicator material 11 in FIG. 2, the non-woven fabric 3 had a high-density portion 3c and a low-density portion 3d both impregnated with the oily substance. Through both the high-density portion 3c and the low-density portion 3d, the deep blue color of the resin layer 2 could be visually recognized from the side of the non-woven fabric 3 as a support.

Figure 3:
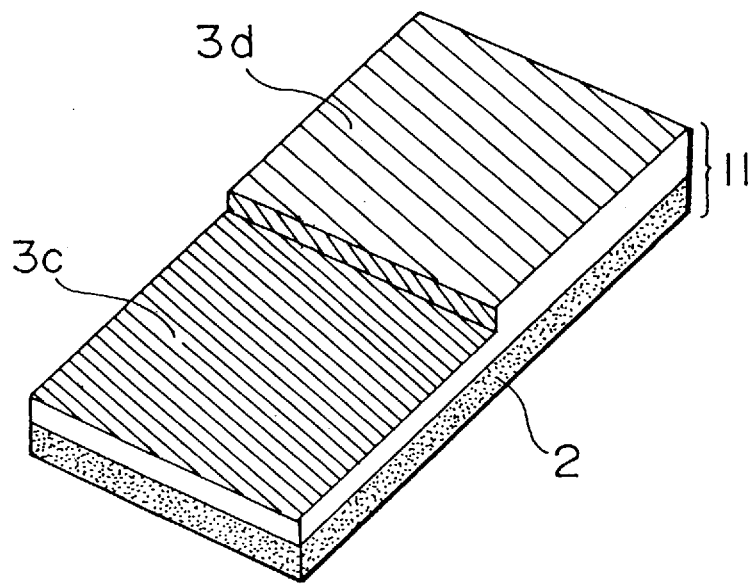
FIG. 3 is a perspective view which schematically shows a partial discoloration state on the indicator material II prepared in Example 30 at a time of its use.

When the above indicator material 11 was allowed to stand horizontally in a room, the low-density portion 3d of the non-woven fabric 3 altered from deep blue to blue with the dissipation of the isobutyl acetate, while the high-density portion 3c of the non-woven fabric 3 kept on showing deep blue, as shown in FIG. 3. When the indicator material was allowed to stand further, the low-density portion 3d of the non-woven fabric 3 altered from blue to light blue, and on the other hand, the high-density portion 3c of the non-woven fabric 3 altered from deep blue to blue. When the indicator material was further allowed to stand, the low-density portion 3d of the non-woven fabric 3 altered from light blue to white, and the dissipation of the isobutyl acetate from that portion nearly came to and end. On the other hand, the high-density portion 3c of the non-woven fabric 3 altered from blue to light blue. When the aroma of the isobutyl acetate disappeared at a final step, the color of entire surface of the non-woven fabric 3 altered to the original color of white.

Further, when the indicator material 11 was slantly placed or suspended perpendicularly, it was found that the color change of the high-density portion 3c and the color change of the low-density portion 3d took place one after the other as described above.

As described above, in the above indicator material 11, the stepwise color change from blue to white through light blue took place in a left half and a right half of the non-woven fabric 3 one after the other, so that the degrees of color changes could be confirmed on the basis of comparisons, and the degree of dissipation of the oily substance (isobutyl acetate) could be clearly shown. Further, the above indicator material 11 could be set regardless of a setting site and a setting method.

EXAMPLE 31
(Preparation of indicator material II)

A non-woven fabric-resin laminate was prepared in the same manner as in Example 30, and then, by an offset printing method, a print portion of characters of "Replace" was formed on the high-density portion of the non-woven fabric constituting the above non-woven fabric-resin laminate in a light blue color which was similar to, but had a lower intensity than, the color of the resin layer. And, a print portion of characters of "in use" was formed on the low-density portion in a deep blue color by an offset printing method. Then, the above non-woven fabric was impregnated with isobutyl acetate in the same manner as in Example 1 to give an indicator material II.

At a stage where the impregnation with isobutyl acetate was completed, the above-prepared indicator material II was in a state in which the deep blue color of the resin layer was clearly visually recognizable from the non-woven fabric layer side, the characters of "in use" were not visually recognizable since they were of a color similar to that of the resin layer, and further, the characters of "Replace" were not visually recognizable, either, since they were in light blue. When the indicator material II was horizontally placed in a room, the low-density portion of the non-woven fabric altered from deep blue to blue with the dissipation of the isobutyl acetate, and the characters of "In use" became recognizable. At this stage, the high-density portion of the non-woven fabric kept on showing a deep blue color, and the characters of "Replace" were in a state in which they were not visually recognized. Then, when a time further passed, the low-density portion of the non-woven fabric altered from blue to light blue, and the high-density portion of the non-woven fabric altered from deep blue to blue. At this stage, the characters of "Replace" were still in a state in which they were not visually recognized. Thereafter, when a time further passed, the low-density portion of the non-woven fabric altered from light blue to white, the original color of the non-woven fabric, and on the other hand, the high-density portion of the non-woven fabric altered from blue to light blue. Then, when the isobutyl acetate disappeared at a final step, the color of entire surface of the non-woven fabric altered to white, the original color of the non-woven fabric so that the characters of "In use" in light blue and the characters of "Replace" in deep blue came into a state where they were recognizable.

Further, when the indicator material II was slantly placed or perpendicularly suspended, it was found that the color change of the high-density portion and the color change of the low-density portion took place one after the other as described above.

As described above, in the above indicator material II, the stepwise color change from blue to white through light blue took place in a left half and a right half of the non-woven fabric one after the other, so that the degrees of color changes could be confirmed on the basis of comparisons, and the degree of dissipation of the oily substance (isobutyl acetate) could be clearly shown. Further, since the characters of "Replace" were not shown before the effect of the aromatic agent (isobutyl acetate) lost its effect, the exchange time can be clearly recognized. Further, the above indicator material II could be set regardless of a setting site and a setting method.

Example 32
(Preparation of indicator material II)

A non-woven fabric-resin laminate was prepared in the same manner as in Example 30, and then, by an offset printing method, a print portion of characters of "Replace" was formed on the high-density portion of the non-woven fabric constituting the above non-woven fabric-resin laminate in a light blue color. And, a print portion of characters of "in use" was formed on the low-density portion in a white color by an offset printing method. Then, the above non-woven fabric was impregnated with isobutyl acetate in the same manner as in Example 1 to give an indicator material II.

In the above-prepared indicator material II, at a stage where the impregnation with isobutyl acetate was completed, the deep blue color of the resin layer was clearly visually recognizable from the non-woven fabric layer side, the characters of "in use" were visually recognizable since they were in white. Further, the characters of "Replace" were not visually recognizable, since they were in light blue. When the indicator material II was horizontally placed in a room, the low-density portion of the non-woven fabric altered from deep blue to blue with the dissipation of the isobutyl acetate. At this stage, the characters of "In use" were also in a recognizable state. On the other hand, the high-density portion of the non-woven fabric kept on showing a deep blue color, and the characters of "Replace" were in a state in which they were not visually recognized. Then, when a time further passed, the low-density portion of the non-woven fabric altered from blue to light blue, and the high-density portion of the non-woven fabric altered from deep blue to blue. At this stage, the characters of "Replace" were still in a state in which they were not visually recognized. Thereafter, when a time further passed, the low-density portion of the non-woven fabric altered from light blue to white, so that the characters of "In use" became indecipherable. On the other hand, the high-density portion of the non-woven fabric altered from blue to light blue. Then, when the isobutyl acetate disappeared at a final step, the color of entire surface of the non-woven fabric altered to white, and the characters of "Replace" came into a state where they were recognizable.

Further, when the indicator material II was slantly placed or perpendicularly suspended, it was found that the color change of the high-density portion and the color change of the low-density portion took place one after the other as described above.

As described above, in the above indicator material II, the stepwise color change from blue to white through light blue took place in a left half and a right half of the non-woven fabric one after the other, so that the degrees of color changes could be confirmed on the basis of comparisons, and the degree of dissipation of the oily substance (isobutyl acetate) could be clearly shown. Further, since the characters of "Replace" were not shown before the effect of the aromatic agent (isobutyl acetate) lost its effect, and since the characters of "In use" disappeared when the aromatic agent (isobutyl acetate) lost its effect, the exchange time could be clearly shown. Further, the above indicator material II could be set regardless of a setting site and a setting method.

EXAMPLE 33
(Preparation of indicator material II)

A non-woven fabric as a support was prepared from 50 parts by weight of an acrylic resin (supplied by Mitsubishi Rayon Co., Ltd., 2$d$, 3 mm) and 50 parts by weight of a heat-fusible fiber (NBF-E, supplied by Daiwabo, 3 d, 5 mm) by a wet paper making method using an inclined paper machine. The prepared non-woven fabric had a basis weight of 50 g/m$^2$ and a density of 0.1 g/cm$^3$.

About a half of the surface of the above non-woven fabric was pressed with a press roll to increase the density of that portion, whereby a high-density portion and a low-density portion were formed in the non-woven fabric. The high-density portion formed by the above pressing had a density of 0.3 g/cm$^3$ and the low-density portion (portion not pressed) had a density of 0.1 g/cm$^3$. The non-woven fabric showed the original color of white.

A resin layer was formed on one surface of the above non-woven fabric in the same manner as in Example 1 to prepare a non-woven fabric-resin laminate. Then, the non-woven fabric of the non-woven fabric-resin laminate was impregnated with isobutyl acetate in the same manner as in Example 1 to give an indicator material II.

The above-obtained indicator material II was determined or evaluated for performances as an indicator material to show that, like the indicator material II obtained in Example 30, it could be set regardless of a setting site and a setting method and that it could clearly show not only the time of expiration of the oily substance (isobutyl acetate) but also the degree of dissipation of the oily substance (isobutyl acetate) with the passage of time.

EXAMPLE 34
(Preparation of indicator material II)

A non-woven fabric-resin laminate was prepared in the same manner as in Example 33, and then, the non-woven fabric of the non-woven fabric-resin laminate was impregnated with empenthrin which was a liquid mothproofing agent (oily mothproofing agent volatile at room temperature) in the same manner as in Example 1, to give an indicator material II.

The above-obtained indicator material II was determined or evaluated for performances as an indicator material to show that, like the indicator material II obtained in Example 30, it could be set regardless of a setting site and a setting method and that it could clearly show not only the time of expiration of the oily substance (empenthrin) but also the degree of dissipation of the oily substance (empenthrin) with the passage of time.

EXAMPLE 35

A non-woven fabric as a support was prepared from 50 parts by weight of an acrylic resin (supplied by Mitsubishi Rayon Co., Ltd., 3$d$, 3 mm) and 50 parts by weight of a heat-fusible fiber (NBF-E, supplied by Daiwabo, 3$d$, 5 mm) in the same manner as in Example 33. The prepared non-woven fabric had a basis weight of 50 g/m$^2$.

The portion, which was nearly a central portion of the non-woven fabric when viewed from the above, was circularly and perpendicularly pressed to increase the density of that portion, whereby a high-density portion and a low-density portion were formed in the non-woven fabric. The high-density portion formed by the above pressing had a density of 0.3 g/cm$^3$ and the low-density portion (portion not pressed) had a density of 0.09 g/cm$^3$. The non-woven fabric showed the original color of white.

A resin layer was formed on one surface of the above non-woven fabric in the same manner as in Example 1 to prepare a non-woven fabric-resin laminate. Then, the non-woven fabric of the non-woven fabric-resin laminate was impregnated with 100 g/m$^2$ of a thyme oil (one oily mothproofing agent) as an oily substance volatile at room temperature in the same manner as in Example 1 to give an indicator material II.

Figure 4:
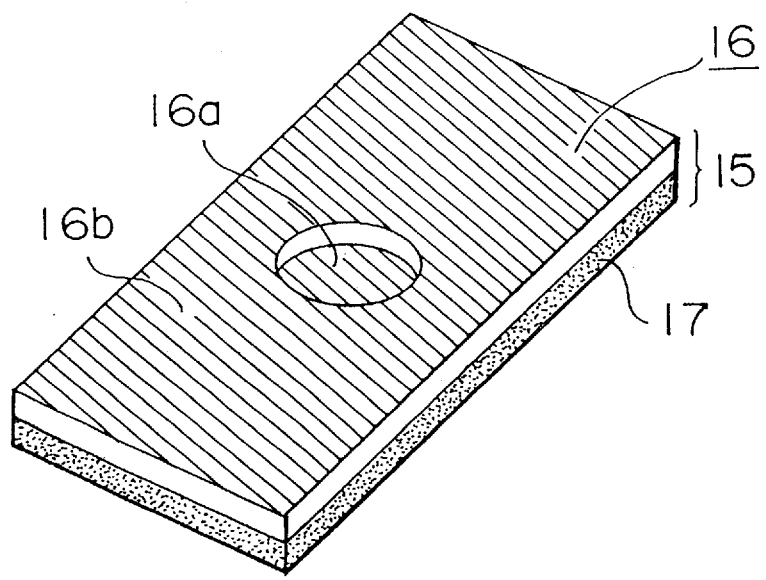
FIG. 4 is a schematic perspective view of an indicator material II prepared in Example 35.

As shown in FIG. 4, in the above indicator material 15, the non-woven fabric 16 had the high-density portion 16$a$ and the low-density portion 16$b$ both impregnated with the oily substance. The high-density portion 16$a$ of the non-woven fabric 16 showed a circular form when viewed from above, and the high-density portion 16 was located nearly in the central portion of the non-woven fabric 16 when viewed from above. On the other hand, the low-density portion 16$b$ of the non-woven fabric 16 was located around the high-density portion 16$a$, and the low-density portion 16$b$ surrounded the high-density portion 16$a$. Through both the high-density portion 16$a$ and the low-density portion 16$b$, the deep blue color of the resin layer 17 formed on one surface of the non-woven fabric 16 could be clearly visually recognized from the side of the non-woven fabric 16 as a support.

In the above indicator material 15, the thyme oil (not shown in FIG. 4) used for the impregnation of the non-woven fabric 16 were dissipated from both the high-density portion 16$a$ and the low-density portion 16$b$, while the thyme oil with which the low-density portion 16b had been impregnated shifted into the high-density portion 16a spontaneously and effectively with the dissipation of the thyme oil from the high-density portion 16a. Therefore, when the observation was made toward the resin layer 17 side from the non-woven fabric 16 side, the high-density portion 16a was visually recognized in deep blue for a long period of time. Further, even after the low-density portion 16b became visually recognized in white after the thyme oil in the low-density portion 16b disappeared (although the color of the resin layer 17 was visually recognized in a light color), the high-density portion 16a was visually recognized in deep blue, while the high-density portion 16a rapidly altered to white.

It was found that the color change of the high-density portion 16a and the color change of the low-density portion 16b took place one after the other as described above even if the above indicator material 15 was horizontally placed, slantly placed or perpendicularly suspended. When the indicator material 15 was perpendicularly suspended, however, puddles of the oily substance (thyme oil) formed to some extent.

In the above indicator material 15, the degree of color change with the dissipation of the oily substance (thyme oil) differed to a great extent between the high-density portion 16a and the low-density portion 16b as described above, and the indicator material 15 could more clearly show the degree of the oily substance (thyme oil). Further, the indicator material 15 could be used regardless of a setting site and a setting method.

As explained in detail in Examples and Comparative Examples, the indicator material I and the indicator material II of the present invention can clearly show not only the time of expiration of the oily substance but also the degree of dissipation of the oily substance which occurs with the passage of time, regardless of a setting site and a setting method.

Further, the indicator material using, as a support, the non-woven fabric containing a fine-denier fiber having a size of 2 denier or less can contain a relatively large amount of the oily substance.

We claim:

1. An indicator material provided by forming a resin layer having a surface partly or wholly colored on one surface of a support formed of a non-woven fabric comprising a fine-denier fiber having a size of 2 denier or less said support and having a low refractive index to light, and impregnating the support with an oily substance volatile at ambient temperature or higher temperature, wherein the resin layer observed from the support side is shifted from a visible state to a support-masked state by the dissipation of the oily substance which occurs with the passage of time.

2. The indicator material of claim 1, wherein the non-woven fabric as a support contains 9 to 100% by weight of the fine-denier fiber having a size of 2 denier or less.

3. The indicator material of claim 1, wherein the non-woven fabric as a support contains 20 to 100% by weight of the fine-denier fiber having a size of 2 denier or less.

4. The indicator material of claim 1, wherein the non-woven fabric as a support contains a fine-denier fiber having a size of 1 denier or less.

5. The indicator material of claim 1, wherein the non-woven fabric as a support has a density of 0.1 to 0.5 g/cm$^3$.

6. The indicator material of claim 1, wherein the non-woven fabric as a support has a non-woven fabric space volume of at least 50 cm$^3$/m$^2$.

7. The indicator material of claim 1, wherein the non-woven fabric as a support is a non-woven fabric prepared by a wet paper making method.

8. The indicator material of claim 1, wherein the non-woven fabric as a support contains a heat-fusible fiber.

9. The indicator material of claim 1, wherein the resin layer is a thermoplastic resin coating whose surface is partly or wholly colored.

10. The indicator material of claim 1, wherein the resin layer has a surface partly or wholly colored by a printing method.

11. The indicator material of claim 1, wherein the indicator material has a print portion showing the termination of dissipation of the oily substance, which print portion is formed on a surface of the non-woven fabric opposite to the surface provided with the resin layer, in a color which has a lower intensity than, and is similar to, a colored portion of the resin layer.

12. The indicator material of claim 1, wherein the indicator material has a print portion showing upon dissipation of the oily substance, which is formed on a surface opposite to the surface provided with the resin layer, in a color similar to a color of the non-woven fabric.

13. The indicator material of claim 1, 11 or 12, wherein the oily substance is an oily mothproofing agent or insecticide volatile at ambient temperature or higher temperature.

14. The indicator material of claim 13, wherein the oily mothproofing agent or insecticide is an evaporable pyrethroid-containing insecticide.

15. An indicator material prepared by forming a resin layer having a surface partly or wholly colored on one surface of a support formed of a non-woven fabric having a partly altered density and having a low refractive index to light, and impregnating the support with an oily substance volatile at ambient temperature or higher temperature, wherein the resin layer observed from the support side is shifted from a visible state to a support-masked state by the dissipation of the oily substance which occurs with the passage of time.

16. The indicator material of claim 15, wherein a portion having a relatively high density is surrounded by a portion having a relatively low density in the non-woven fabric as a support.

17. The indicator material of claim 15, wherein the non-woven fabric as a support is a non-woven fabric having a partly altered density obtained by partly pressing a non-woven fabric having a substantially uniform density.

18. The indicator material of claim 15, wherein the non-woven fabric as a support contains a fine-denier fiber having a size of 2 denier or less.

19. The indicator material of claim 15, wherein the non-woven fabric as a support contains 9 to 100% by weight of a fine-denier fiber having a size of 2 denier or less.

20. The indicator material of claim 15, wherein the non-woven fabric as a support contains 20 to 100% by weight of a fine-denier fiber having a size of 2 denier or less.

21. The indicator material of claim 15, wherein the non-woven fabric as a support contains a fine-denier fiber having a size of 1 denier or less.

22. The indicator material of claim 15, wherein the non-woven fabric as a support contains a heat-fusible fiber.

23. The indicator material of claim 15, wherein the non-woven fabric as a support is a non-woven fabric obtained by partly altering a density of a non-woven fabric prepared by a wet paper making method.

24. The indicator material of claim 15, wherein the resin layer is a thermoplastic resin coating partly or wholly colored.

25. The indicator material of claim 15, wherein the resin layer has a surface partly or wholly colored by a printing method.

26. The indicator material of claim 15, wherein a print portion showing the termination of dissipation of the oily substance is formed on a high-density portion on a surface opposite to the surface provided with the resin layer, in a color which has a lower intensity than, and is similar to, a colored portion of the resin layer.

27. The indicator material of claim 15, wherein a print portion showing upon dissipation of the oily substance is formed on a surface on the non-woven fabric opposite to the surface provided with the resin layer, in a color which has a higher intensity than or an intensity equivalent to, and is similar to, a colored portion of the resin layer, or in a color similar to the non-woven fabric.

28. The indicator material of claim 27, wherein the print portion is formed on a low-density portion of the non-woven fabric.

29. The indicator material of claim 15, 26 or 27, wherein the oily substance is an oily mothproofing agent or insecticide volatile at ambient temperature or higher temperature.

30. The indicator material of claim 29, wherein the oily mothproofing agent or insecticide is an evaporable pyrethroid-containing insecticide.

31. The indicator material claim 1, wherein the non-woven fabric has a partly altered density.

* * * * *